(12) United States Patent
Gibson et al.

(10) Patent No.: US 7,894,916 B2
(45) Date of Patent: Feb. 22, 2011

(54) INSERTION TOOL FOR A COCHLEAR IMPLANT ELECTRODE ARRAY

(75) Inventors: Peter Gibson, New South Wales (AU); Ian Darley, New South Wales (AU); Claudiu Treaba, New South Wales (AU); John Parker, New South Wales (AU); Fysh Dadd, New South Wales (AU)

(73) Assignee: Cochlear Limited, Macquarie University, NSW (AU)

( * ) Notice: Subject to any disclaimer, the term of this patent is extended or adjusted under 35 U.S.C. 154(b) by 618 days.

(21) Appl. No.: 10/203,079

(22) PCT Filed: Oct. 17, 2001

(86) PCT No.: PCT/AU01/01312
§ 371 (c)(1),
(2), (4) Date: Nov. 18, 2002

(87) PCT Pub. No.: WO02/32498
PCT Pub. Date: Apr. 25, 2002

(65) Prior Publication Data
US 2003/0093139 A1    May 15, 2003

(30) Foreign Application Priority Data

| Oct. 17, 2000 | (AU) | ................................ 0807 |
| Oct. 17, 2000 | (AU) | ................................ 0808 |
| Oct. 25, 2000 | (AU) | ................................ 1005 |
| Nov. 29, 2000 | (AU) | ................................ 1778 |

(51) Int. Cl.
*A61N 1/05* (2006.01)
(52) U.S. Cl. .......................... 607/137; 607/57
(58) Field of Classification Search ............... 607/137, 607/57, 56, 55
See application file for complete search history.

(56) References Cited

U.S. PATENT DOCUMENTS 3,890,977 A    6/1975    Wilson
(Continued)

FOREIGN PATENT DOCUMENTS

EP    0002068    5/1979
(Continued)

OTHER PUBLICATIONS

International Search Report PCT/AU01/01312; dated Dec. 19, 2001; Applicant: Cochlear Limited; Inventors: Hauser et al.
(Continued)

*Primary Examiner*—Niketa I Patel
*Assistant Examiner*—Alyssa M Alter
(74) *Attorney, Agent, or Firm*—Kilpatrick Stockton LLP

(57) ABSTRACT

A cochlear implant electrode assembly device (10) comprising an elongate electrode carrier member (11), and a shape element (15) formed of a memory material, such as Nitinol. The elongate member (11) is made of a resiliently flexible first material and has a length and a plurality of electrodes (12) mounted thereon adapted to apply a preselected tissue stimulation. The elongate member (11) has a pre-formed curved orientation that at least substantially matches an inside surface of a cochlea, an implantable orientation different to said pre-formed orientation that allows said member to be inserted into an implantee's cochlea, and an at least one intermediate orientation between said implantable orientation and said pre-formed orientation. The shape element (15) is removably positioned within the elongate member (11) and extends along at least a portion of the length thereof. The shape element (15) has a first shape selected for biasing the elongate member (11) into the implantable orientation when the shape element is at a first temperature, and at least a second shape that allows the elongate member (11) to adopt said at least one intermediate orientation when the shape element (15) is exposed to a temperature of the cochlea (30) being different than the first temperature.

39 Claims, 2 Drawing Sheets

U.S. PATENT DOCUMENTS

| | | | |
|---|---|---|---|
| 4,033,331 A | 7/1977 | Guss et al. | |
| 4,046,151 A | 9/1977 | Rose | |
| 4,154,247 A | 5/1979 | O'Neill | |
| 4,306,563 A | 12/1981 | Iwatschenko | |
| 4,357,497 A | 11/1982 | Hochmair et al. | |
| 4,381,013 A | 4/1983 | Dutcher | |
| 4,532,930 A | 8/1985 | Crosby et al. | |
| 4,762,135 A | 8/1988 | van der Puije et al. | |
| 4,994,069 A | 2/1991 | Ritchart et al. | |
| 5,025,799 A | 6/1991 | Wilson | |
| 5,554,114 A | 9/1996 | Wallace et al. | |
| 5,571,160 A | 11/1996 | Nyman | |
| 5,645,585 A | 7/1997 | Kuzma | |
| 5,653,742 A * | 8/1997 | Parker et al. | 607/137 |
| 5,755,765 A | 5/1998 | Hyde et al. | |
| 5,762,630 A | 6/1998 | Bley et al. | |
| 5,769,077 A | 6/1998 | Lindegren | |
| 5,902,329 A | 5/1999 | Hoffmann et al. | |
| 5,957,996 A | 9/1999 | Shiraishi | |
| 6,038,484 A | 3/2000 | Kuzma | |
| 6,119,044 A * | 9/2000 | Kuzma | 607/137 |
| 6,195,586 B1 | 2/2001 | Kuzma | |
| 6,304,787 B1 | 10/2001 | Kuzma et al. | |
| 6,309,410 B1 | 10/2001 | Kuzma et al. | |
| 6,421,569 B1 * | 7/2002 | Treaba et al. | 607/137 |
| 6,968,238 B1 | 11/2005 | Kuzma | |
| 7,050,858 B1 | 5/2006 | Kuzma et al. | |
| 7,146,227 B2 | 12/2006 | Dadd et al. | |
| 7,269,461 B2 | 9/2007 | Dadd et al. | |
| 7,272,449 B2 | 9/2007 | Dadd et al. | |
| 2003/0045921 A1 | 3/2003 | Dadd et al. | |
| 2003/0181967 A1 | 9/2003 | Dadd et al. | |
| 2004/0030376 A1 | 2/2004 | Gibson et al. | |
| 2004/0078057 A1 | 4/2004 | Gibson | |
| 2004/0116995 A1 | 6/2004 | Dadd | |
| 2004/0122501 A1 | 6/2004 | Dadd et al. | |
| 2007/0073371 A1 | 3/2007 | Dadd et al. | |
| 2008/0004684 A1 | 1/2008 | Dadd et al. | |
| 2008/0269864 A1 | 10/2008 | Dadd et al. | |

FOREIGN PATENT DOCUMENTS

| | | |
|---|---|---|
| EP | 0350188 | 1/1990 |
| EP | 0602859 | 6/1994 |
| EP | 0653223 | 5/1995 |
| EP | 0739642 | 10/1996 |
| EP | 0773037 | 5/1997 |
| EP | 0778043 | 6/1997 |
| EP | 0778044 | 6/1997 |
| EP | 0783900 | 7/1997 |
| EP | 0783901 | 7/1997 |
| EP | 0784994 | 7/1997 |
| EP | 0784995 | 7/1997 |
| EP | 0919254 | 6/1999 |
| GB | 2217993 A | 11/1989 |
| WO | 9710784 | 3/1997 |
| WO | 9911321 | 3/1999 |
| WO | 9956810 | 11/1999 |
| WO | 0033909 | 6/2000 |
| WO | 0071063 | 11/2000 |
| WO | 0228473 | 4/2002 |
| WO | 0228474 | 4/2002 |
| WO | 0232498 | 4/2002 |

OTHER PUBLICATIONS

International Preliminary Examination Report PCT/AU01/01312; dated Feb. 13, 2002; Applicant: Cochlear Limited; Inventors: Hauser et al.

International Search Report issued by International Searching Authority in connection with International Patent Application No. PCT/AU2001/001230, dated Oct. 26, 2001 (4 pages).

International Preliminary Examination Report issued by International Preliminary Examining Authority in connection with International Patent Application No. PCT/AU2001/001230, dated Nov. 27, 2001 (3 pages).

International Search Report issued by International Searching Authority in connection with International Patent Application No. PCT/AU2001/001231, dated Oct. 26, 2001 (3 pages).

International Preliminary Examination Report issued by International Preliminary Examining Authority in connection with International Patent Application No. PCT/AU2001/001231, dated Nov. 20, 2001 (3 pages).

International Search Report issued by International Searching Authority in connection with International Patent Application No. PCT/AU2001/001312, dated Dec. 19, 2001 (3 pages).

International Preliminary Examination Report issued by International Preliminary Examining Authority in connection with International Patent Application No. PCT/AU2001/001312, dated Feb. 13, 2002 (4 pages).

International-type Search Report issued by the Australian Patent Office in connection with Australian Patent Application No. PR 0541, dated Dec. 20, 2000 (2 pages).

International-type Search Report issued by the Australian Patent Office in connection with Australian Patent Application No. PR 0542, dated Dec. 20, 2000 (3 pages).

International-type Search Report issued by the Australian Patent Office in connection with Australian Patent Application No. PR 0684, dated Dec. 20, 2000 (3 pages).

International-type Search Report issued by the Australian Patent Office in connection with Australian Patent Application No. PR 0807, dated Dec. 20, 2000 (3 pages).

International-type Search Report issued by the Australian Patent Office in connection with Australian Patent Application No. PR 1005, dated Dec. 20, 2000 (3 pages).

Australian Intellectual Property Office, "Examiner's First Report," issued in connection with Australian Patent Application No. 93501/01, dated Aug. 25, 2004 (1 page).

Australian Intellectual Property Office, "Examiner's First Report," issued in connection with Australian Patent Application No. 95246/01, dated Aug. 16, 2004 (2 pages).

Canadian Intellectual Property Office, "Notice of a Requisition by Examiner," issued in connection with Canadian Patent Application No. 2,392,996, dated Nov. 24, 2008 (3 pages).

European Patent Office, "Communication with Supplemental Search Report," issued in connection with European Patent Application No. 01973835.0, dated Jan. 22, 2004 (3 pages).

European Patent Office, "Communication pursuant to Article 96(2) EPC," issued in connection with European Patent Application No. 01973835.0, dated May 10, 2004 (3 pages).

European Patent Office, "Communication under Rule 51(4) EPC," issued in connection with European Patent Application No. 01973835.0, dated Dec. 21, 2004 (30 pages).

European Patent Office, "Communication under Rule 51(4) EPC," issued in connection with European Patent Application No. 01973835.0, dated Jan. 20, 2005 (30 pages).

European Patent Office, "Communication under Rule 51(4) EPC," issued in connection with European Patent Application No. 01973835.0, dated Feb. 8, 2005 (30 pages).

European Patent Office, "Communication under Rule 51(4) EPC," issued in connection with European Patent Application No. 01973835.0, dated Feb. 25, 2005 (30 pages).

European Patent Office, "Decision to Grant a European Patent pursuant to Article 97(2) EPC," issued in connection with European Patent Application No. 01973835.0, dated Jul. 28, 2005 (2 pages).

European Patent Office, "Supplementary European Search Report," issued in connection with European Patent Application No. 01975835.8, dated May 15, 2009 (3 pages).

European Patent Office, "Communication under Rule 71(3) EPC," issued in connection with European Patent Application No. 01975835.8, dated Nov. 30, 2009 (31 pages).

European Patent Office, "Decision to Grant a European Patent pursuant to Article 97(1) EPC," issued in connection with European Patent Application No. 01975835.8, dated Apr. 22, 2010 (2 pages).

European Patent Office, "Decision to Grant a European Patent pursuant to Article 97(1) EPC," issued in connection with European Patent Application No. 01975875.4, dated Mar. 25, 2010 (2 pages).

"Epicardial-Transvenous Left Ventricular Lead with Dual Ring Electrodes (Cathode Ring and Anode Ring) Design," Research Disclosure, pp. 790-791, No. 403, Kenneth Mason Publications Ltd, Hampshire, England, Nov. 1997 (4 pages).

"Epicardial-Transvenous Left Atrial Lead with Wound 'Butterfly Tongue' Electrode," Research Disclosure, p. 785, No. 403, Kenneth Mason Publications Ltd, Hampshire, England, Nov. 1997 (3 pages).

Australian Examiner's First Report on Australian Patent Application No. 95286/01, dated Sep. 27, 2004.

Austrialian Notice of Acceptance of Australian Patent Application No. 95286/01, dated Dec. 20, 2004.

Canadian Examiner's Report for Canadian Patent Application 2,400,729, dated Nov. 21, 2008.

Supplementary European Search Report for European Patent Application No. 01975875, dated Apr. 29, 2009.

Translation of a Notice of Reasons for Rejection from the Japanese Patent Office for Japanese Patent Application No. 2002-535734, dated Sep. 12, 2006.

* cited by examiner

INSERTION TOOL FOR A COCHLEAR IMPLANT ELECTRODE ARRAY

This application is a National Stage Application under 35 USC §371(c) of PCT Application No. PCT/AU2001/001312, entitled "INSERTION TOOL FOR A COCHLEAR IMPLANT ELECTRODE ARRAY," filed Oct. 17, 2001, which claims priority to Australian Provisional Application No. PR 0808, filed Oct. 17, 2000, Australian Provisional Application No. PR 0807, filed Oct. 17, 2000, Australian Provisional Application No. PR 1005, filed Oct. 25, 2000, and Australian Provisional Application No. PR 1778, filed Nov. 29, 2000.

FIELD OF THE INVENTION

The present invention relates to an implantable device and, in particular, to all implantable cochlear electrode assembly.

BACKGROUND OF THE INVENTION

Hearing loss, which may be due to many different causes, is generally of two types, conductive and sensorineural. Of these types, conductive hearing loss occurs where the normal mechanical pathways for sound to reach the hair cells in the cochlea are impeded, for example, by damage to the ossicles. Conductive hearing loss may often be helped by use of conventional hearing aid systems, which amplify sound so that acoustic information does reach the cochlea and the hair cells.

In many people who are profoundly deaf, however, the reason for deafness is sensorineural hearing loss. This type of hearing loss is due to the absence of, or destruction of, the hair cells in the cochlea which transduce acoustic signals into nerve impulses. These people are thus unable to derive suitable benefit from conventional hearing aid systems, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532,930, the contents of which are incorporated herein by reference, provides a description of one type of traditional cochlear implant system.

Cochlear implant systems have typically consisted of two key components, namely all external component commonly referred to as a processor unit, and an implanted internal component commonly referred to as a stimulator/receiver unit. Traditionally, both of these components have cooperated together to provide the sound sensation to an implantee.

The external component has traditionally consisted of a microphone for detecting sounds, such as speech and environmental sounds, a speech processor that converts the detected sounds and particularly speech into a coded signal, a power source such as a battery, and an external antenna transmitter coil.

The coded signal output by the speech processor is transmitted transcutaneously to the implanted stimulator/receiver unit situated within a recess of the temporal bone of the implantee. This transcutaneous transmission occurs through use of an inductive coupling provided between the external antenna transmitter coil which is positioned to communicate with an implanted antenna receiver coil provided with the stimulator/receiver unit. This communication serves two essential purposes, firstly to transcutaneously transmit the coded sound signal and secondly to provide power to the implanted stimulator/receiver unit. Conventionally, this link has been in the form of a radio frequency (RF) link, but other such links have been proposed and implemented with varying degrees of success.

The implanted stimulator/receiver unit typically included the antenna receiver coil that receives the coded signal and power from the external processor component, and a stimulator that processes the coded signal and outputs a stimulation signal to an intracochlea electrode assembly which applies the electrical stimulation directly to the auditory nerve producing a hearing sensation corresponding to the original detected sound.

The external componentry of the cochlear implant has been traditionally carried on the body of the implantee, such as in a pocket of the implantee's clothing, a belt pouch or in a harness, while the microphone has been mounted on a clip mounted behind the ear or on a clothing lapel of the implantee.

More recently, due in the main to improvements in technology, the physical dimensions of the speech processor have been able to be reduced allowing for the external componentry to be housed in a small unit capable of being worn behind the ear of the implantee. This unit has allowed the microphone, power unit and the speech processor to be housed in a single unit capable of being discretely worn behind the ear, with the external transmitter coil still positioned on the side of the user's head to allow for the transmission of the coded sound signal from the speech processor and power to the implanted stimulator unit.

Together with improvements in available technology much research has been undertaken in the area of understanding the way sound is naturally processed by the human auditory system. With such an increased understanding of how the cochlea naturally processes sounds of varying frequency and magnitude, there is a need to provide an improved cochlear implant system that delivers electrical stimulation to the auditory nerve in a way that takes into account the natural characteristics of the cochlea.

It is known in the art that the cochlea is tonotopically mapped. In other words, the cochlea can be partitioned into regions, with each region being responsive to signals in a particular frequency range. This property of the cochlea is exploited by providing the electrode assembly with all array of electrodes, each electrode being arranged and constructed to deliver a cochlea stimulating signal within a preselected frequency range to the appropriate cochlea region. The electrical currents and electric fields from each electrode stimulate the cilia disposed on the modiola of the cochlea. Several electrodes may be active simultaneously.

It has been found that in order for these electrodes to be effective, the magnitude of the currents flowing from these electrodes and the intensity of the corresponding electric fields, are a function of the distance between the electrodes and the modiola. If this distance is relatively great, the threshold current magnitude must be larger than if the distance is relatively small. Moreover, the current from each electrode may flow in all directions, and the electrical fields corresponding to adjacent electrodes may overlap, thereby causing cross-electrode interference. In order to reduce the threshold stimulation amplitude and to eliminate cross-electrode interference, it is advisable to keep the distance between the electrode array and the modiola as small as possible. This is best accomplished by providing the electrode array in the shape which generally follows the shape of the modiola. Also, this way the delivery of the electrical stimulation to the auditory nerve is most effective as the electrode contacts are as close to the auditory nerves that are particularly responsive to selected pitches of sound waves.

In order to achieve this electrode array position close to the inside wall of the cochlea, the electrode needs to be designed in such a way that it assumes this position upon or immediately following insertion into the cochlea. This is a challenge as the array needs to be shaped such that it assumes a curved shape to conform with the shape of the modiola and must also be shaped such that the insertion process causes minimal trauma to the sensitive structures of the cochlea. In this sense it has been found to be desirable for the electrode array be generally straight during the insertion procedure.

Several procedures have been adopted to provide an electrode assembly that is relatively straightforward to insert while adopting a curved configuration following insertion in the cochlea. In one case, a platinum wire stylet is used to hold a pre-curved electrode array in a generally straight configuration up until insertion. Following insertion, the platinum stylet is withdrawn allowing the array to return to its pre-curved configuration.

In another development, a bimetallic filament (such as nickel/titanium) or a filament made of a nickel/titanium alloy is positioned in the electrode assembly and used to again hold a pre-curved electrode array in a generally straight configuration while the array is at about room temperature. On insertion into the body and exposure to body temperature, the filament bends into a pre-selected curved configuration.

In a still further arrangement, a longitudinal element that is arranged on one side of the array and constructed to change its dimension on insertion can be utilised. For example, the longitudinal element could include a hydrogel such as polyacrylic acid (PAA) which expands after insertion by absorbing water from the cochlear fluid.

In developing such electrode array designs, it is of great importance that the design be constructed to minimise potential damage to sensitive structures in the cochlear on insertion and placement. Each of the above constructions suffer from a number of disadvantages in this regard.

Still further, it has been proposed to straighten pre-curved electrode arrays using inserted longitudinal elements or surrounding sheaths formed from bioresorbable materials that dissolve or soften on implantation. A disadvantage with use of such bioresorbable materials is that, due to the generally wet nature of the surgical environment, the polymer can dissolve or soften before the electrode array is appropriately positioned.

U.S. Pat. No. 6,119,044 provides a description of another arrangement adapted to ensure electrode contacts of an implantable array are against the modiolar wall of the cochlea following implantation. In this arrangement, a positioning wire made from memory wire is positioned in a longitudinal channel of the array. On insertion into the cochlea and exposure to body temperature, the positioning wire is adapted to adopt a curved spiral shape which causes the electrode contacts to be forced against the modiolar wall.

In this arrangement, the positioning wire serves to maintain the electrode array in its spiral configuration following implantation and provides a permanent bending force to the electrode array to ensure that the spiral configuration is adopted. A disadvantage of this arrangement is that should for any reason the array require replacement or removal, such an arrangement would be difficult to remove without causing damage to the delicate structures of the cochlea.

The present invention is directed to an electrode assembly adapted to overcome some of the difficulties of prior art electrode assemblies.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to a first aspect, the present invention is an implantable tissue-stimulating device comprising:

an elongate member made of a resiliently flexible first material and having a length and a plurality of electrodes mounted thereon adapted to apply a preselected tissue stimulation, the elongate member having a pre-formed orientation, an implantable orientation different to said pre-formed orientation that allows said member to be inserted into an implantee's body, and an at least one intermediate orientation between said implantable and said pre-formed orientation; and a shape element removably positioned within the elongate member and extending along at least a portion of the length thereof, said element having:
  a first shape selected for biasing said elongate member into said implantable orientation when the shape element is at a first temperature; and
  at least a second shape that allows the elongate member to adopt said at least one intermediate orientation when the shape element is exposed to a pre-determined temperature different than said first temperature.

In a preferred embodiment of this aspect, the pre-formed orientation of the elongate member is curved. More preferably, the elongate member adopts a spiral curvature when in the pre-formed orientation.

According to a second aspect, the present invention is a cochlear implant electrode assembly device comprising:

an elongate electrode carrier member made of a resiliently flexible first material and having a length and a plurality of electrodes mounted thereon adapted to apply a preselected tissue stimulation, the elongate member having a pre-formed curved orientation that at least substantially matches an inside surface of a cochlea, an implantable orientation different to said pre-formed orientation that allows said member to be inserted into an implantee's cochlea, and an at least one intermediate orientation between said implantable orientation and said pre-formed orientation; and a shape element removably positioned within the elongate member and extending along at least a portion of the length thereof, said element having:
  a first shape selected for biasing said elongate member into said implantable orientation when the shape element is at a first temperature; and
  at least a second shape that allows the elongate member to adopt said at least one intermediate orientation when the shape element is exposed to a temperature of the cochlea being different than said first temperature.

In this invention, the shape element biases the elongate member in the implantable orientation and serves to prevent the elongate member adopting its preferred pre-formed orientation, such as the pre-formed curved orientation defined in the second aspect. This is in contrast to the situation described in U.S. Pat. No. 6,119,044 where the positioning wire is adapted to control the orientation of the flexible carrier in all orientations.

In a preferred embodiment of each aspect, the shape element is formed from a shape memory material. The shape memory material is preferably relatively stiffer than the first material. In one embodiment, the shape memory material can be a nickel-titanium alloy or Nitinol. In another embodiment, the shape memory material can be a plastics material or made from another non-metal shape memory material. In a preferred embodiment, the shape memory material of the shape element is used to hold the elongate member of the electrode array in a generally straight orientation while the array is at about room temperature or at least a temperature different to body temperature (about 37° C.). On insertion into the body and exposure to body temperature, the shape element adopts the second shape. In one embodiment, the second shape allows the elongate member to adopt a curved orientation in which the tip of the elongate member has adopted at least a degree of curvature.

In a preferred embodiment, the shape element is removable from the elongate member once the elongate member has adopted its said at least one intermediate orientation. On removal of the shape element, the elongate member preferably adopts its pre-formed orientation.

The elongate member is preferably preformed from a plastics material with memory. The elongate member preferably has a first end that is firstly inserted into the implantee.

In a preferred embodiment, the implantable orientation is preferably substantially straight. More preferably, the implantable orientation is straight.

In a preferred embodiment, the elongate member is formed from a suitable biocompatible material. In one embodiment, the biocompatible material can be a silicone, such as a flexible silicone elastomer-Silastic. Silastic MDX 4-4210 is an example of one suitable silicone for use in the formation of the elongate member. In another embodiment, the elongate member call be formed from a polyurethane or similar material.

In a further embodiment, the elongate member can have a resiliently flexible tip member extending forwardly from the first end of the body. The tip member preferably has a distal end and a proximal end. The tip member call have a stiffness that is relatively less stiff than said stiffening element. The tip member can further be formed of a material that is substantially the same or the same stiffness as the body of the elongate member. In another embodiment, the tip member can be formed of a material that is relatively less stiff than at least a portion of the elongate member. In a further embodiment, the tip member call be formed of a material that undergoes a change in stiffness, preferably a decrease in stiffness, on insertion into the body, such as the cochlea.

In a further embodiment, the stiffness of the tip member can vary along at least a portion of its length from its distal end to its proximal end. In one embodiment, the stiffness of the tip member can vary over the entire length of the tip member or only a portion thereof. The stiffness can increase from the distal end to the proximal end. In one embodiment, the stiffness of the tip member over said portion or its length can increase gradually from its distal end towards to the proximal end. The increase in stiffness can be substantially smooth or increase in a stepwise fashion.

In a further embodiment, the tip member can be formed of the same material as the body of the elongate member. In another embodiment, the tip member can be formed of a different material to that of the body of the elongate member. The tip member can be comprised of an inner relatively stiff core of material having a tapered end, with at least the tapered end being overlaid by a relatively flexible material that extends beyond the tapered end of the core material so that the tip member undergoes a gradual decrease in flexibility in the region of the tapered end of the core moving away from the distal end.

The tip member can be formed separately to the body of the elongate member and mounted thereto. For example, the tip member call be adhered to the first end of the body of the elongate member. In another embodiment, the tip member can be integrally formed with the body of the elongate member. The tip member can be formed from a silicone material. In another embodiment, the tip member can be formed of an elastomeric material, such as polyurethane.

In another embodiment, the tip member can have a plurality of metallic particles dispersed therethrough. The metallic particles can be substantially evenly dispersed through the tip member. Alternatively, the metallic particles can be non-evenly dispersed throughout the tip member. In one embodiment, the metallic particles can increase in density away from the distal end towards the proximal end of the tip member. By varying the density of the metallic particles, it is possible to vary the relative stiffness of the tip member.

The metallic particles preferably comprise a biocompatible material, such as platinum. The particles can be substantially spherical or spherical. It will be appreciated that the particles can have other suitable shapes. In one embodiment, the particles can have a diameter between about 50 µm and 100 µm.

In addition to, or instead of, being used to potentially modify the physical characteristics of the tip member, the provision of the metallic particles also result in the tip member being detectable by fluoroscopy and X-ray techniques. This provides another means for the surgeon to monitor the placement and position of the tip member during or after insertion of the electrode array in the body, such as in the cochlea.

When the elongate member is in the first configuration, the tip member is preferably substantially straight and, more preferably, straight.

In a further embodiment, the tip member can be coated with a lubricious material. The lubricious material can be a bioresorbable or non-bioresorbable material.

The tip member can be formed from, or incorporate as a portion thereof, a bioresorbable material. The presence of the bioresorbable material preferably results in the flexibility of the tip member increasing on insertion of the tip member into the body, such as the cochlea. The bioresorbable material in the tip member can be selected from the group consisting of polyacrylic acid (PAA), polyvinyl alcohol (PVA), polylactic acid (PLA) and polyglycolic acid (PGA).

In another embodiment, the tip member can be formed from, or incorporate as a portion thereof, a polymeric coating which becomes softer, and so increases in resilient flexibility, in the presence of moisture or body heat. The tip member preferably has a length from its distal end to its proximal end in the range of about 0.3 to 4 mm, more preferably about 1.0 to 3.0 mm. The diameter of the tip member can be substantially constant for a majority of its length or can vary in diameter. The tip member can be substantially cylindrical, cylindrical, or non-cylindrical for a majority of its length. At the distal end, the diameter preferably gradually decreases to form a rounded end. The maximum diameter of the tip member is preferably about 0.55 mm.

In one embodiment, the tip member can be solid. In another embodiment, the tip member can have an external wall defining a cavity. In one embodiment, the cavity can have a diameter greater than that of the receiving portion of the body of the elongate member. In a further embodiment, the cavity can extend from the proximal end towards the distal end of the tip member. The cavity can decrease in diameter away from the proximal end. The cavity can be in communication with a distal end of the receiving portion of the body of the elongate member. In a further embodiment, the stiffening means can extend into the cavity when positioned within the device or assembly according to the respective aspects of the present invention. In a preferred embodiment, the tip member can move relative to the stiffening means when it extends into the cavity of the tip member.

In general, the tip could be made of a combination of materials arranged in a variety of geometries depending on the specific design goal. The outside shape and size of the tip can also be made in a variety of forms depending on the design goal.

In one embodiment, the shape element can be removably positioned in a lumen extending through the elongate member for at least a portion of its length. In one embodiment, the lumen extends through the elongate member for a substantial portion of its length. In a further embodiment, the lumen extends from an opening distal the first end to or adjacent the first end. The shape element preferably extends the entire length of the lumen in the elongate member.

The lumen can be cylindrical or have another cross-sectional shape. The shape element can extend out of the opening allowing the element to be manipulated and removed from the lumen during insertion of the device.

The shape element can also be cylindrical, such as a wire, or could have another cross-sectional shape, such as oval, rectangular, triangular and others. The shape element could also be tapered along its length to achieve graduation in stiffness and strength, or have other non-uniform cross-sectional shapes along its length to achieve particular desirable bending characteristics.

In a further embodiment, the elongate member can have an outer layer. The outer layer can act as a stiffening sheath for the elongate member. The stiffening sheath can be formed of a bioresorbable material which dissolves or softens on exposure to a fluid. The stiffening sheath can dissolve or soften on exposure to a saline solution or a body fluid of the implantee, such as cochlear fluid.

In a further embodiment, the bioresorbable material of the stiffening sheath is selected from the group comprising polyacrylic acid (PAA), polyvinyl alcohol (PVA), polylactic acid (PLA) and polyglycolic acid (PGA). It is also envisaged that other suitable materials could be used.

The device can include all additional layer surrounding the stiffening sheath. The additional layer can have a first rate of fluid ingress therethrough and have at least one fluid ingress means formed therein, the rate of fluid ingress through the fluid ingress means being greater than the first rate of fluid ingress through the additional layer.

The fluid ingress means can comprise one or more openings in the additional layer. The openings can be closable. The openings can comprise slits in the additional layer. The slits can be formed to allow substantially the same or the same rate of ingress of fluid through the additional layer. In another embodiment, at least one slit can allow a different rate of progress of fluid through the additional layer compared to the other slits.

The purpose of allowing the elongate member to adopt the intermediate orientation, following insertion into the cochlea, is to enable the elongate member to be inserted into the cochlea in a way which minimises trauma to the walls of the cochlea. The preferred shape of this intermediate orientation is for the elongate member to assume a shape that is more curved than the straight orientation present upon insertion. By having the previously straight array adopt a more curved shape, the elongate member is guided to adopt a mid-scala trajectory as it is inserted into the cochlea. This ensures that as the elongate member is carefully inserted deeper into the spiral shaped cochlea, the intermediate curved orientation assists in ensuring that the elongate member can be inserted deep into the cochlea without causing excessive trauma to the walls of the cochlea.

On subsequent removal of the shape element, the elongate member is free to adopt the fully curved pre-formed orientation desired of an implant for final position in the cochlea.

The present invention provides a surgeon with a means to at least partially control the rate of curvature formation in a cochlear electrode assembly during insertion into the cochlea. Such increased control is envisaged to reduce the potential for trauma to the cochlea caused by electrode assembly insertion. The present invention also provides a means of assisting the insertion process of the electrode assembly into the cochlea by allowing the electrode assembly to alter its orientation during the insertion process to allow for more desirable cochlea penetration and/or electrode positioning.

In a further embodiment, at least a portion of an outer surface of the elongate member can have a coating of a lubricious material. In one embodiment, a substantial portion or the entire outer surface of the elongate member can have a coating of the lubricious material.

In this embodiment, the lubricious material can be selected from the group comprising polyacrylic acid (PAA), polyvinyl alcohol (PVA), polylactic acid (PLA) and polyglycolic acid (PGA). It is envisaged that other similar materials could also be used.

In a further aspect, the present invention comprises a method of implanting a tissue-stimulating device or cochlear electrode assembly device as defined herein in a body of an implantee.

In this aspect, the method can comprise a step of accessing the implantation site and then a step of inserting the device. Prior to insertion, the device is preferably substantially straight or straight. On insertion, the elongate member can adopt an intermediate orientation (as defined herein). Following full insertion and after removal of the shape element, the device has preferably adopted its pre-formed orientation.

Once implanted, the electrodes can receive stimulation signals from a stimulator means. The stimulator means is preferably electrically connected to the elongate member by way of an electrical lead. The lead can include the one or more wires extending from each electrode of the array mounted on the elongate member.

In one embodiment, the lead can extend from the elongate member to the stimulator means or at least the housing thereof. In one embodiment, the lead is continuous with no electrical connectors, at least external the housing of the stimulator means, required to connect the wires extending from the electrodes to the stimulator means. One advantage of this arrangement is that there is no requirement for the surgeon implanting the device to make the necessary electrical connection between the wires extending from the electrodes and the stimulator means.

The stimulator means is preferably positioned within a housing that is implantable within the implantee. The housing for the stimulator means is preferably implantable within a recess in the bone behind the ear posterior to the mastoid.

When implanted, the housing preferably contains, in addition to the stimulator means, a receiver means. The receiver means is preferably adapted to receive signals from a controller means. The controller means is, in use, preferably mounted external to the body of the implantee such that the signals are transmitted transcutaneously through the skin of the implantee.

Signals can preferably travel from the controller means to the receiver means and vice versa. The receiver means can include a receiver coil adapted to receive radio frequency (RF) signals from a corresponding transmitter coil worn externally of the body. The radio frequency signals can comprise frequency modulated (FM) signals. While described as a receiver coil, the receiver coil can preferably transmit signals to the transmitter coil which receives the signals.

The transmitter coil is preferably held in position adjacent the implanted location of the receiver coil by way of respective attractive magnets mounted centrally in, or at some other position relative to, the coils.

The external controller can comprise a speech processor adapted to receive signals output by a microphone. During use, the microphone is preferably worn on the pinna of the implantee, however, other suitable locations can be envisaged, such as a lapel of the implantee's clothing. The speech processor encodes the sound detected by the microphone into a sequence of electrical stimuli following given algorithms, such as algorithms already developed for cochlear implant systems. The encoded sequence is transferred to the implanted stimulator/receiver means using the transmitter and receiver coils. The implanted stimulator/receiver means demodulates the FM signals and allocates the electrical pulses to the appropriate attached electrode by an algorithm which is consistent with the chosen speech coding strategy.

The external controller further comprises a power supply. The power supply can comprise one or more rechargeable batteries. The transmitter and receiver coils are used to provide power via transcutaneous induction to the implanted stimulator/receiver means and the electrode array.

While the implant system can rely on external componentry, in another embodiment, the controller means, including the microphone, speech processor and power supply can also be implantable. In this embodiment, the controller means can be contained within a hermetically sealed housing or the housing used for the stimulator means.

BRIEF DESCRIPTION OF THE DRAWINGS

By way of example only, a preferred embodiment of the invention is now described with reference to the accompanying drawings, in which.

PREFERRED MODE OF CARRYING OUT THE INVENTION

Figure 1:
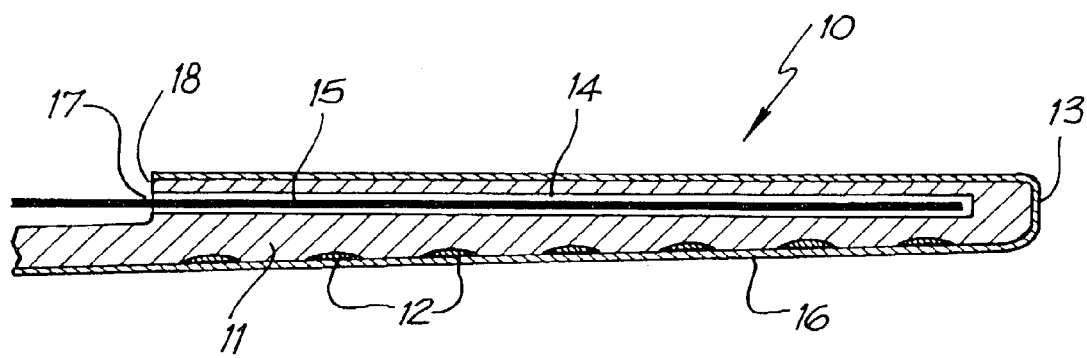
FIG. 1 is a simplified cross-sectional view of one embodiment of an electrode assembly according to the present invention depicted in its implantable orientation.

One embodiment of a cochlear implant electrode assembly according to the present invention is depicted generally as 10 in the drawings.

The depicted electrode assembly 10 has an electrical lead extending back to a stimulator/receiver housing. In considering this invention, it is to be understood that each electrode 12 may have one or more wires (not depicted) electrically connected thereto and extending from each respective electrode 12 back through the lead to the stimulator/receiver.

The assembly 10 comprises an elongate electrode carrier member 11 having a plurality of electrodes 12 mounted thereon. For the purposes of clarity, the electrodes 12 depicted in FIG. 1 are not necessarily shown to scale. A larger number of electrodes than that depicted in FIG. 1 can also be envisaged. The electrodes 12 are not depicted in FIGS. 2 and 3 for reasons of clarity.

The depicted elongate member 11 is preformed from a resiliently flexible silicone with memory and is preformed to a curved orientation suitable for insertion in the scale tympani 31 of a patient's cochlea 30. The elongate member 11 has a first end 13 that is firstly inserted into the cochlea 30 upon insertion of the assembly 10.

Figure 4:
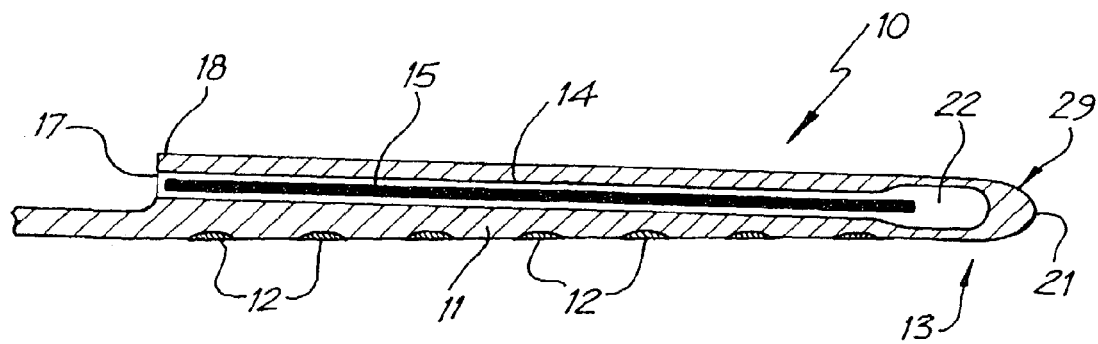
FIG. 4 is a simplified cross-sectional view of another embodiment of an electrode assembly according to the present invention.

As depicted in FIG. 4, the elongate member 11 can have a tip member 29, having a different construction to that depicted in FIG. 1, which is integrally formed with its first end 13. The tip 29 is formed from the same silicone used to fabricate the elongate member 11 and, in the depicted embodiment, the material of tip member 29 has a resilient flexibility equal to that of the material used for the carrier member 11.

Figure 5A:
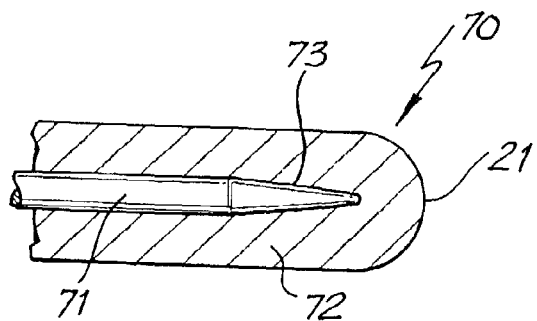
FIGS. 5a-5d depict alternative tip structures for the electrode assembly depicted in FIG. 4.

Possible alternative constructions for the tip member 29 are provided in FIGS. 5a-5d. As depicted in FIG. 5a, the tip member 70 can be solid and formed of an inner core 71 of relatively stiff material 71 and an outer layer 72 of relatively flexible material. The core 71 can taper in diameter over region 73 towards the distal end 21. The taper 73 causes the overall stiffness of the tip 70 to increase over the length of the taper 73 away from the distal end 21. The outer layer 72 can be formed of the same material as the remainder of the body of the elongate carrier member 11 or can be a different material.

Figure 5B:
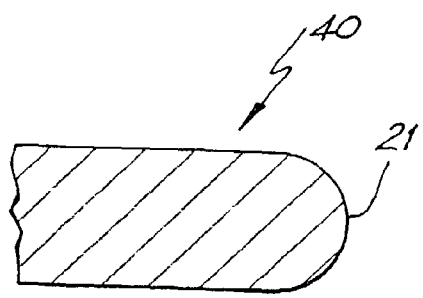

As depicted in FIG. 5b, the tip member 40 can comprise a solid mass integrally formed to the first end 13 of the elongate carrier 11.

Figure 5C:
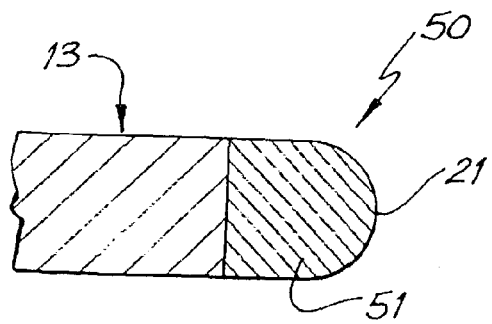

Still further and as depicted in FIG. 5c, the tip member 50 can comprise a solid mass 51 that is formed separately from the carrier member 11 and subsequently adhered thereto.

Figure 5D:
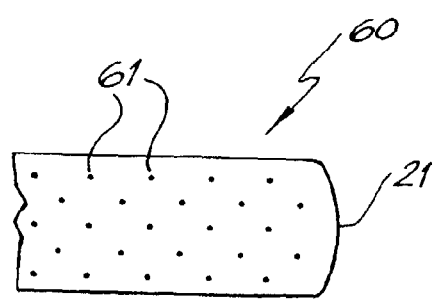

As depicted in FIG. 5d, the tip member 60 can comprise an elastomeric silicone material having a plurality of substantially spherical platinum particles 61 dispersed therethrough. The particles 61 have a diameter between about 50 μm and 100 μm. It will be appreciated that the particles 61 depicted in FIG. 6d are not drawn to scale.

In FIG. 5d, the particles 61 are depicted as substantially evenly dispersed through the tip member 60. In another embodiment, the particles could be non-evenly dispersed through the tip member. For example, the particles could increase in density away from the distal end 21 towards the proximal end of the tip member 60. By varying the density of the platinum particles 61, it is possible to vary the relative stiffness of the tip member 60.

In addition to, or instead of, being used to potentially modify the physical characteristics of the tip member, the provision of the metallic particles 61 also result in the tip member 60 being detectable by fluoroscopy and X-ray techniques. This provides another means for the surgeon to either monitor the placement and position of the tip member 60 during or after insertion of the electrode array 10 in an implantee's cochlea.

Disposed within a lumen 14 is a nickel/titanium (Nitinol™) wire 15. In the depicted embodiment, the wire 15 alone has a stiffness that is sufficient to retain the silicone elongate member 11 in a straight orientation when the wire 15 is at room temperature (as shown in FIG. 1).

Whilst a substantially cylindrical lumen is depicted, the lumen 14 could indeed be any shape necessary to perform the function. The wire 15 has a circular cross-section. Other shape elements having different cross sections and forms can be envisaged.

Figure 2:
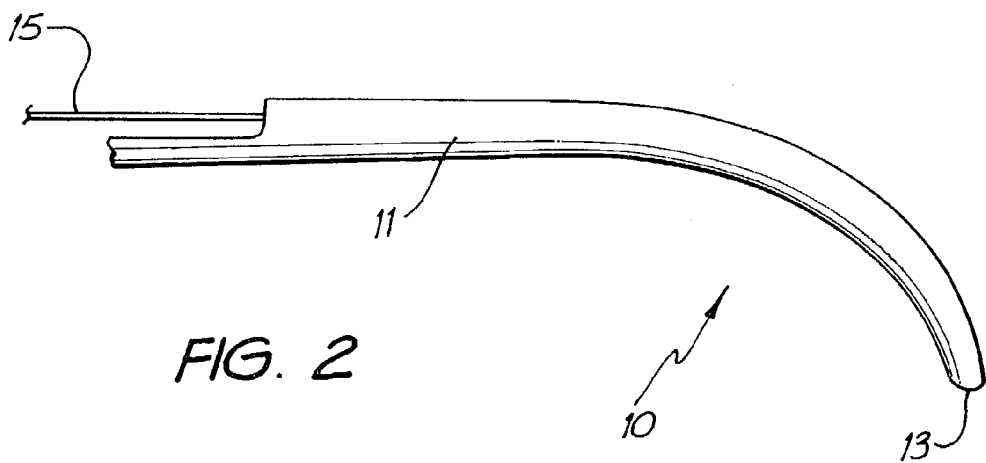
FIG. 2 is a simplified side elevational view of the electrode assembly of FIG. 1 depicted in an intermediate orientation.

As depicted in FIG. 2, the wire has a preferred direction of curl on exposure to body temperature within the cochlea. In one embodiment, the array 10 can have an indicia means that provides an indication to a user, such as a surgeon, of the of the preferred direction of curl of the array on implantation. This is important as the array 10 needs to be oriented in the cochlea such that the direction of curl results in the array 10 being able to be moved into the scala tympani 31. The indicia means can comprise a loop formed in the wire at or adjacent a distal end thereof. The loop as well as acting as an indicia means can act as a means of engaging with and withdrawing the wire 15 from the lumen 14 during or following implantation. In one embodiment, the loop can be in the same plane as the preferred direction of curl of the wire 15. The loop could extend away from the preferred direction of curl of the wire 15.

In the embodiment shown in FIG. 1, overlaying the depicted elongate member 11 it is possible to provide a sheath 16 of bioresorbable and lubricious material. The bioresorbable material of the depicted stiffening sheath is PAA that is adapted to dissolve on exposure to cochlear fluids. Other suitable bioresorbable materials can be envisaged and such materials need not necessarily dissolve on exposure to fluids. For example, the sheath can be made of a material that softens upon exposure to fluids but does not get absorbed.

While the elongate member 11 is manufactured with a preformed curved orientation, the assembly 10 is typically delivered to a surgeon with the Nitinol wire 15 in place. The wire 15, while at room temperature, holds the elongate member 11 in the straight orientation depicted in FIG. 1.

Upon insertion into the scala tympani 31 of the cochlea 30, the exposure of the assembly 10 to body temperature (about 37° C.) results in the Nitinol wire 15 adopting a curved orientation. As the wire 15 adopts the curved orientation, the elongate member 11 is free to also adopt the curved orientation as is depicted in FIG. 2.

Figure 3:
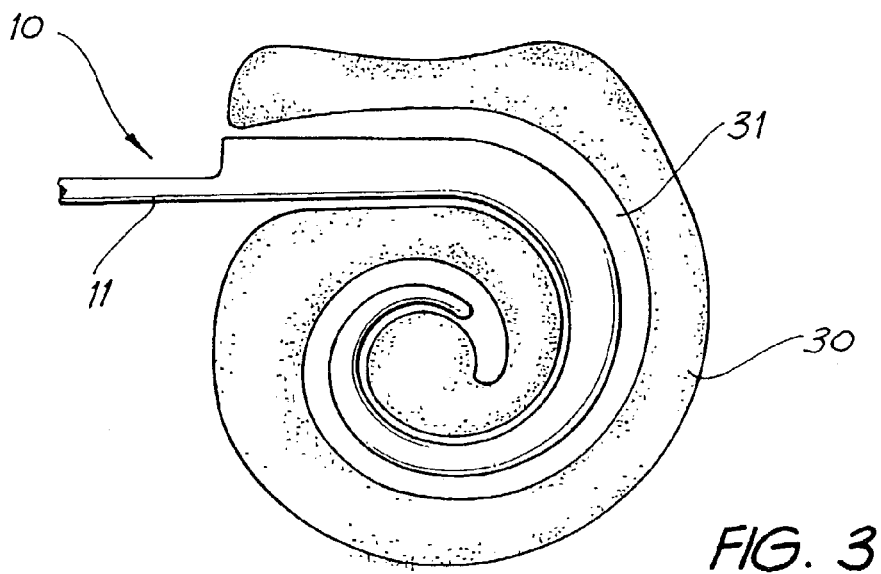
FIG. 3 is a simplified part-sectional, part side elevational view of the electrode assembly depicted in its pre-formed orientation following insertion in the cochlea.

As the elongate member 11 curls, the surgeon can continue to further insert the assembly 10 into the scala tympani 31. During the further insertion process, the surgeon can commence withdrawal of the wire 15 through opening 17 of the lumen 14 at end 18. Alternatively, the surgeon may withdraw the wire 15 following complete insertion of the assembly into its final position, this decision being dependent of the surgeon's preferences. Upon withdrawal of the wire 15, the elongate member 11 is free to adopt its pre-formed spiral orientation (as is depicted in FIG. 3), with the electrodes facing the modiola within the cochlea 30 so that they are positioned as close as possible to the spiral ganglia thereof.

The provision of the shape memory wire 15 provides the surgeon with greater control of the implantation procedure for the cochlear implant electrode assembly 10. The provision of greater control minimises the potential for trauma to the sensitive tissues inside the cochlea and also enhances the likelihood of successful placement of the assembly 10 at the first attempt.

While the preferred embodiment of the invention has been described in conjunction with a cochlear implant, it is to be understood that the present invention has wider application to other implantable electrodes, such as electrodes used with pacemakers.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A cochlear implant comprising:
an elongate shape element configured to maintain a substantially straight configuration when at a first temperature and to curl in response to being at a second temperature greater than the first temperature; and
a resiliently flexible elongate carrier member, having a longitudinally-extending lumen configured to receive the shape element and a plurality of tissue-stimulating electrodes, configured to adopt substantially straight and partially curved configurations in response to biasing forces applied by said shape element positioned in said lumen when said shape element is at said first and second temperatures, respectively, and to adopt a fully curved configuration, in which said carrier member is configured to substantially conform to a modiolus when positioned in a cochlea, in response to said shape element being removed from said lumen;
wherein said shape element is configured to prevent said carrier member from adopting said fully curved configuration when said shape element is at a temperature approximately equal to body temperature and is positioned in said lumen; and
wherein, for said carrier member, said fully curved configuration is more curved than said partially curved configuration, and said partially curved configuration is more curved than said substantially straight configuration.

2. The cochlear implant of claim 1, wherein said elongate carrier member is formed of a first material, and wherein said shape element is formed of a shape memory material that is relatively stiffer than said first material.

3. The cochlear implant of claim 2, wherein said shape memory material comprises at least one plastic material.

4. The cochlear implant of claim 3, wherein said shape memory material is Nitinol.

5. The cochlear implant of claim 1, wherein said second temperature is approximately equal to body temperature.

6. The cochlear implant of claim 1, wherein said elongate carrier member is preformed from a biocompatible plastic material.

7. The cochlear implant of claim 6, wherein said biocompatible plastic material is selected from the group comprising a silicone, and a polyurethane.

8. The cochlear implant of claim 1, wherein said lumen extends through a substantial portion of said elongate carrier member from an opening at a proximal end of said carrier member to a distal end of said carrier member.

9. The cochlear implant of claim 1, wherein said shape element is configured to extend out from said elongate carrier member, when said shape element is disposed in said lumen, allowing said shape element to be manipulated and removed from said carrier member during insertion of said carrier member.

10. The cochlear implant of claim 1, wherein said plurality of tissue-stimulating electrodes are mounted along a surface of said elongate carrier member configured to face the modiolus when the carrier member is inserted in the cochlea.

11. The cochlear implant of claim 1, wherein said elongate carrier member further comprises an outer layer configured to act as a stiffening sheath for said carrier member.

12. The cochlear implant of claim 11, wherein said stiffening sheath is formed of a bioresorbable material configured to dissolve or soften on exposure to a fluid.

13. The cochlear implant of claim 12, wherein said bioresorbable material is selected from the group comprising polyacrylic acid (PAA), polyvinyl alcohol (PVA), polylactic acid (PLA) and polyglycolic acid (PGA).

14. The cochlear implant of claim 12, wherein the cochlear implant further comprises:
   an additional layer surrounding said stiffening sheath configured to have a first rate of fluid ingress therethrough; and
   at least one opening formed in said additional layer having a rate of fluid ingress therethrough that is greater than said first rate of fluid ingress through said additional layer.

15. The cochlear implant of claim 14, wherein said at least one opening in said additional layer is constructed and arranged to be closable so as to substantially prevent fluid ingress therethrough.

16. The cochlear implant of claim 1, wherein at least a portion of an outer surface of said elongate carrier member has a coating of a lubricious material.

17. The cochlear implant of claim 16, wherein said lubricious material is selected from the group comprising polyacrylic acid (PAA), polyvinyl alcohol (PVA), polylactic acid (PLA) and polyglycolic acid (PGA).

18. The cochlear implant of claim 1, wherein a resiliently flexible tip member extends forwardly from a distal end of said elongate carrier member.

19. The cochlear implant of claim 18, wherein said tip member has a plurality of metallic particles dispersed therethrough.

20. An implantable medical device comprising:
   a cochlear implant comprising:
      an elongate shape element configured to maintain a substantially straight configuration when at a first temperature and to curl in response to being at a second temperature greater than the first temperature; and
      a resiliently flexible elongate carrier member, having a longitudinally-extending lumen configured to receive the shape element and a plurality of tissue-stimulating electrodes, configured to adopt substantially straight and partially curved configurations in response to biasing forces applied by said shape element positioned in said lumen when said shape element is at said first and second temperatures, respectively, and to adopt a fully curved configuration, in which said carrier member is configured to substantially conform to a modiolus when positioned in a cochlea, in response to said shape element being removed from said lumen;
      wherein said shape element is configured to prevent said carrier member from adopting said fully curved configuration when said shape element is at a temperature approximately equal to body temperature and is positioned in said lumen; and
      wherein, for said carrier member, said fully curved configuration is more curved than said partially curved configuration, and said partially curved configuration is more curved than said substantially straight configuration.

21. The implantable medical device of claim 20, wherein said elongate carrier member is formed of a first material, and wherein said shape element is formed of a shape memory material that is relatively stiffer than said first material.

22. The implantable medical device of claim 21, wherein said shape memory material comprises at least one plastic material.

23. The implantable medical device of claim 22, wherein said shape memory material is Nitinol.

24. The implantable medical device of claim 20, wherein said second temperature is approximately equal to body temperature.

25. The implantable medical device of claim 20, wherein said elongate carrier member is preformed from a biocompatible plastic material.

26. The implantable medical device of claim 25, wherein said biocompatible plastic material is selected from the group comprising a silicone, and a polyurethane.

27. The implantable medical device of claim 20, wherein said lumen extends through a substantial portion of said elongate carrier member from an opening at a proximal end of said carrier member to a distal end of said carrier member.

28. The implantable medical device of claim 20, wherein said shape element is configured to extend out from said elongate carrier member, when said shape element is disposed in said lumen, allowing said shape element to be manipulated and removed from said carrier member during insertion of said carrier member.

29. The implantable medical device of claim 20, wherein said plurality of tissue-stimulating electrodes are mounted along a surface of said elongate carrier member configured to face the modiolus when the carrier member is inserted in the cochlea.

30. The implantable medical device of claim 20, wherein said elongate carrier member further comprises an outer layer configured to act as a stiffening sheath for said carrier member.

31. The implantable medical device of claim 30, wherein said stiffening sheath is formed of a bioresorbable material configured to dissolve or soften on exposure to a fluid.

32. The implantable medical device of claim 31, wherein said bioresorbable material is selected from the group comprising polyacrylic acid (PAA), polyvinyl alcohol (PVA), polylactic acid (PLA) and polyglycolic acid (PGA).

33. The implantable medical device of claim 31, wherein the cochlear implant further comprises:
   an additional layer surrounding said stiffening sheath configured to have a first rate of fluid ingress therethrough; and
   at least one opening formed in said additional layer having a rate of fluid ingress therethrough that is greater than said first rate of fluid ingress through said additional layer.

34. The implantable medical device of claim 33, wherein said at least one opening in said additional layer is constructed and arranged to be closable so as to substantially prevent fluid ingress therethrough.

35. The implantable medical device of claim 20, wherein at least a portion of an outer surface of said elongate carrier member has a coating of a lubricious material.

36. The implantable medical device of claim 35, wherein said lubricious material is selected from the group comprising polyacrylic acid (PAA), polyvinyl alcohol (PVA), polylactic acid (PLA) and polyglycolic acid (PGA).

37. The implantable medical device of claim 20, wherein a resiliently flexible tip member extends forwardly from a distal end of said elongate carrier member.

38. The implantable medical device of claim 37, wherein said tip member has a plurality of metallic particles dispersed therethrough.

39. A method for implanting a resiliently flexible carrier member of a cochlear implant into a recipient's cochlea, the carrier member having a longitudinally-extending lumen configured to receive an elongate shape element and a plurality of tissue-stimulating electrodes, the shape element configured to maintain a substantially straight configuration when at a first temperature and to curl in response to being at a second temperature greater than the first temperature, the method comprising:

maintaining the shape element at a first temperature when the shape element is positioned in the lumen to maintain the carrier member in a substantially straight configuration;

inserting the carrier member into the recipient's cochlea while the shape element is positioned in the lumen thereby exposing the shape element to a temperature greater than the first temperature and approximately equal to body temperature and thereby causing the shape element to bias the carrier member into a partially curved configuration that is more curved than the substantially straight configuration;

preventing the carrier member from adopting a fully curved configuration that is more curved than the partially curved configuration via the shape element positioned in the lumen when the shape element is at the temperature approximately equal to body temperature; and removing the shape element from the lumen thereby allowing the carrier member to adopt the fully curved configuration, and thereby allowing the carrier member to substantially conform to a modiolus of the cochlea.

\* \* \* \* \*